United States Patent [19]
Mandeville, III et al.

[11] Patent Number: 5,925,379
[45] Date of Patent: Jul. 20, 1999

[54] INTERPENETRATING POLYMER NETWORKS FOR SEQUESTRATION OF BILE ACIDS

[75] Inventors: W. Harry Mandeville, III, Lynnfield; Stephen Randall Holmes-Farley, Arlington; Thomas X. Neenan, Boston; George M. Whitesides, Newton, all of Mass.

[73] Assignee: GelTex Pharmaceuticals, Inc., Waltham, Mass.

[21] Appl. No.: 08/826,197

[22] Filed: Mar. 27, 1997

[51] Int. Cl.$^6$ ............................ A61K 9/10; A61K 47/32
[52] U.S. Cl. ..................... 424/484; 424/486; 424/487; 525/903; 514/824
[58] Field of Search .................. 424/484, 486, 424/487; 525/903; 514/824

[56] References Cited

U.S. PATENT DOCUMENTS

| | | |
|---|---|---|
| 2,874,132 | 2/1959 | Riener . |
| 3,288,770 | 11/1966 | Butler ................................ 260/88.3 |
| 3,562,266 | 2/1971 | Minisci et al. . |
| 3,692,895 | 9/1972 | Nelson et al. ............................ 424/78 |
| 3,780,171 | 12/1973 | Irmscher et al. ......................... 424/79 |
| 3,787,474 | 1/1974 | Daniels et al. ........................ 260/459 |
| 3,801,641 | 4/1974 | Payot et al. . |
| 3,980,770 | 9/1976 | Ingelman et al. ........................ 424/79 |
| 4,027,009 | 5/1977 | Grier et al. .............................. 424/78 |
| 4,071,478 | 1/1978 | Shen et al. ............................. 260/2 R |
| 4,101,461 | 7/1978 | Strop et al. ............................. 521/32 |
| 4,111,859 | 9/1978 | Strop et al. ............................. 521/33 |
| 4,426,489 | 1/1984 | Wessling et al. ...................... 524/815 |
| 4,540,760 | 9/1985 | Harada et al. ......................... 526/211 |
| 4,559,391 | 12/1985 | Ueda et al. ............................ 525/366 |
| 4,605,701 | 8/1986 | Harada et al. ......................... 525/107 |
| 4,680,360 | 7/1987 | Ueda et al. ............................ 526/310 |
| 5,189,111 | 2/1993 | Danner ................................. 525/328.2 |
| 5,374,422 | 12/1994 | St. Pierre et al. .................... 424/78.12 |
| 5,414,068 | 5/1995 | Bliem et al. ............................ 528/288 |
| 5,428,112 | 6/1995 | Ahlers et al. ........................ 525/326.7 |
| 5,430,110 | 7/1995 | Ahlers et al. ........................ 525/328.2 |
| 5,451,397 | 9/1995 | Albright et al. ....................... 424/78.01 |
| 5,462,730 | 10/1995 | McTaggart et al. ................ 424/78.35 |
| 5,580,929 | 12/1996 | Tanaka et al. . |

FOREIGN PATENT DOCUMENTS

| | | |
|---|---|---|
| 0 081 291 A3 | 6/1983 | European Pat. Off. . |
| 0432995A1 | 6/1991 | European Pat. Off. . |
| 798488 | 7/1958 | United Kingdom . |
| WO91/18027 | 11/1991 | WIPO . |
| WO94/27620 | 12/1994 | WIPO . |
| WO 95/19384 | 7/1995 | WIPO . |
| WO95/34585 | 12/1995 | WIPO . |
| WO95/34588 | 12/1995 | WIPO . |

OTHER PUBLICATIONS

Heming, A.E. and Flanagan, Thomas L., "Considerations in the Selection of Cation Exchange Resins for Therapeutic Use, " *Annals of the New York Academy of Sciences*, 57:239–251 (1954).

McCarthy, Peter A., "New Approaches to Atherosclerosis: An Overview," *Medicinal Research Reviews*, 13(2):139–159 (1993).

Butler, G.B. and Do, C.H., "Comblike Cyclopolymers of Alkyldiallylamines and Alkyldiallylmethylammonim Chlorides," in *Water–Soluble Polymers*; eds. Shalaby, McCormick & Butler, Chapter 9, pp. 151–158 ACS Symposium Series 467 (1991).

Wang, G. –J. and Engberts, J., "Study of the Conformational State of Non–Cross–Linked and Cross–Linked Poly(alkylmethyldiallylammonium Chlorides) in Aqueous Solution by Fluorescence Probing," *Gazzetta Chimica Italiana*, 125: 393–397 (1995).

Hodgkin, H. et al., "Use of $^{13}$C–NMR in the Study of Reactions on Crosslinked Resins," Published by John Wiley & Sons, *J. of Polymer Science: Polymer Chemistry Edition*, 19(5) : 1239–1249 (1981).

Sperling, Interpenetrating Polymer Networks, Klempner et al., ed., *American Chemical Society*, Washington, D.C. (1994), Chapter 1.

*Primary Examiner*—Edwards J. Webman
*Attorney, Agent, or Firm*—Hamilton, Brook, Smith & Reynolds, P.C.

[57] ABSTRACT

The present invention relates to a method for removing bile salts from a patient, comprising the step of administering to the patient a therapeutically effective amount of a polymer network composition comprising a cationic polymer. In one embodiment, the polymer network is an interpenetrating polymer network. In another embodiment, the polymer network is a semi-interpenetrating polymer network.

43 Claims, No Drawings

INTERPENETRATING POLYMER NETWORKS FOR SEQUESTRATION OF BILE ACIDS

BACKGROUND OF THE INVENTION

Salts of bile acids act as detergents to solubilize and, consequently, aid in the digestion of dietary fats. Bile acids are derived from cholesterol. Following digestion, bile acids can be passively absorbed or reabsorbed by active transport.

Since bile acids are synthesized from cholesterol, reabsorption of bile acids from the intestine conserves lipoprotein cholesterol. Conversely, cholesterol levels can be reduced by hindering reabsorption of bile acids.

One method of reducing the amount of bile acids that are reabsorbed is oral administration of compounds that sequester the bile acids and cannot themselves be absorbed. The sequestered bile acids consequently are excreted. Cholesterol is then employed to produce more bile acids, thereby lowering the serum cholesterol level of the patient.

Polymers having cationic groups are particularly effective at sequestering bile acids. The efficacy of such polymers can be further improved by the incorporation of hydrophobic groups. However, the simultaneous incorporation of hydrophobic and cationic groups into a single polymer can be a synthetic challenge. Therefore, there is a need for novel bile acid sequestrants which provide an intimate association of cationic and hydrophobic groups in a readily prepared form.

SUMMARY OF THE INVENTION

The present invention relates to a method for removing bile salts from a patient. The method comprises the step of administering to the patient a therapeutically effective amount of a polymer network composition comprising a cationic polymer. The cationic polymer carries a positive charge at physiological pH, and can include amine groups or ammonium groups.

In one embodiment, the polymer network composition further comprises a hydrophobic polymer. The hydrophobic polymer can bear a hydrophobic group, such as a straight chain or branched $C_2$–$C_{24}$-alkyl group, an arylalkyl group or an aryl group. In this embodiment, the invention offers the advantage that cationic and hydrophobic groups can be incorporated into a single polymer composition without being present on a single polymer strand.

The polymer network composition can include an interpenetrating polymer network, wherein each polymer within the network is cross-linked. The polymer network composition can also include an interpenetrating polymer network, wherein at least one polymer within the network is not cross-linked, such as a semi-interpenetrating polymer network.

DETAILED DESCRIPTION OF THE INVENTION

The present invention is based on the discovery that interpenetrating polymer networks comprising cationic groups are useful in the sequestration of bile acids. The present invention provides a method for removing bile salts from a patient, comprising the step of administering to the patient a therapeutically effective amount of a polymer network composition comprising a cationic polymer.

A "therapeutically effective amount" is an amount which is sufficient to remove a significant quantity of bile salts from the patient and to, thus, lower the serum cholesterol level of the patient. The patient can be an animal, for example, a mammal, or a human.

The term "polymer network composition" as used herein, refers to an interpenetrating polymer network or a semi-interpenetrating polymer network comprising two or more polymers. As defined in the art, an interpenetrating polymer network is a combination of two or more cross-linked polymers in network form which are synthesized in juxtaposition to each other (Sperling in *Interpenetrating Polymer Networks*, Klempner et al., ed., American Chemical Society, Washington, D.C. (1994)). A semi-interpenetrating polymer network comprises at least one polymer which is cross-linked and at least one polymer which is not cross-linked. Interpenetrating polymer networks and semi-interpenetrating polymer networks are believed to be formed of at least one cross-linked polymer network, with at least one additional polymer intimately associated with or penetrating the network. The additional polymer can also be in cross-linked network form. Such polymer networks can be distinguished from other multicomponent polymer materials, such as polymer blends, graft copolymers and block copolymers by, among others, their methods of synthesis, as described in Sperling, supra (1994).

The term "cationic polymer", as used herein, refers to a polymer which bears a positive charge at physiological pH. Such a polymer can have cationic or basic groups along the polymer backbone or on the polymer side chains. A basic group is a group which is protonated at physiological pH to form a cationic group. When the polymer network comprises a polymer having basic groups, the polymer network can be administered in the free base form or as the salt of a pharmaceutically acceptable acid. Cationic polymers include polymers which comprise primary, secondary or tertiary amine groups, or acid salts thereof, and/or quaternary ammonium groups. Additional suitable cationic groups include amidino, guanidino, phosphonium, etc. Examples of suitable cationic polymers include polyvinylamine, polyallylamine, polyethyleneimine and polymers characterized by a repeat unit having one of the general formulas shown below:

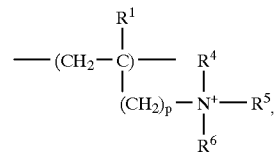

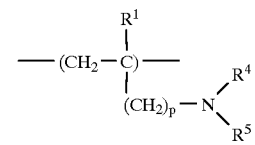

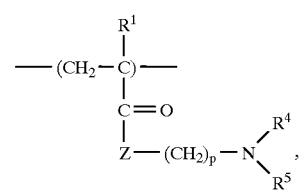

-continued

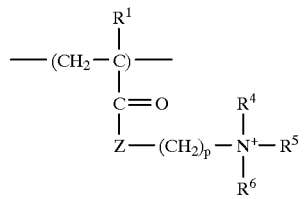

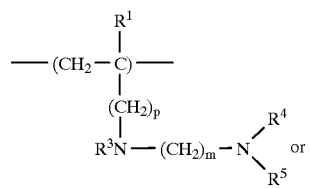

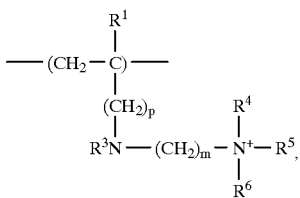

wherein Z is an oxygen atom or an NR$^7$ group, p is an integer from 0 to about 10, m is an integer from 1 to about 10, R$^1$ is hydrogen, methyl or ethyl, R$^3$ and R$^7$ are each, independently, hydrogen or alkyl and R$^4$, R$^5$, and R$^6$ are each, independently, hydrogen, a substituted or unsubstituted alkyl group, preferably a methyl group, or a substituted or unsubstituted arylalkyl group. Suitable alkyl substituents include amino and ammonio groups (primary, secondary, tertiary, or quaternary), halogen atoms, including fluorine, chlorine and bromine atoms; aryl groups, such as phenyl and naphthyl groups; nitro groups, cyano groups, sulfonyl groups, and sulfinyl groups.

Polymer networks comprising ammonium groups or quaternary ammonium groups will be associated with a negatively charged counter ion, preferably the conjugate base of a pharmaceutically acceptable acid. Pharmaceutically acceptable acids include hydrochloric acid, citric acid, tartaric acid, lactic acid, phosphoric acid, methanesulfonic acid, acetic acid, formic acid, maleic acid, fumaric acid, malic acid, succinic acid, malonic acid, sulfuric acid, L-glutamic acid, L-aspartic acid, pyruvic acid, mucic acid, benzoic acid, glucuronic acid, oxalic acid, ascorbic acid and acetylglycine.

In one embodiment, at least a portion of the amino groups in the polymer are substituted with an aminoalkyl or ammonioalkyl group, wherein the alkyl group comprises from about 2 to about 24 carbon atoms. Suitable polymers comprising amino groups substituted with aminoalkyl or ammonioalkyl groups include those which are characterized by a repeat unit of the general formula

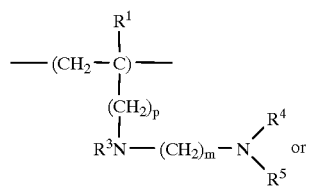

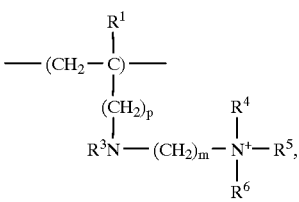

wherein R$^1$, R$^4$, R$^5$, R$^6$, p and m are as defined above, and R$^3$ is hydrogen or alkyl. The polymer bearing such a unit can be a copolymer which, for example, further comprises a repeat unit which does not include the —(CH$_2$)$_m$—N$^{(+)}$R$^4$R$^5$ (R$^6$) unit, i.e. the extent of amino group alkylation is less than 100%.

In one embodiment, the cationic polymer bears a quaternary ammonium group and the hydrophobic polymer is an amine-substituted polymer with a hydrophobic backbone, such as poly(allylamine), poly(vinylamine), poly (ethyleneimine) and the other amine substituted polymers discussed above. The amine-substituted polymer can include one or more amine or quaternary ammonium groups substituted with a C$_2$–C$_{24}$-alkyl group or a C$_2$–C$_{24}$-alkyl derivative. Such polymers include the amine-substituted polymers discussed previously wherein at least a portion of the amino nitrogen atoms are substituted with a normal or branched, unsubstituted or fluorinated C$_2$–C$_{24}$-alkyl group, arylalkyl group, or aryl group.

In a preferred embodiment, the polymer network composition comprises a cationic polymer and a hydrophobic polymer, such as a polymer having a hydrophobic backbone or a polymer comprising pendant hydrophobic groups.

Hydrophobic polymers which are suitable for the composition to be administered are characterized by a hydrophobic backbone or by a monomer or repeat unit having a hydrophobic group, such as a substituted or unsubstituted straight chain or branched alkyl group, an arylalkyl group or an aryl group. Examples of suitable hydrophobic polymers include polymers comprising one or more monomers selected from among N—C$_2$–C$_{24}$-alkylacrylamides, N—C$_2$–C$_{24}$-alkylmethacrylamides, C$_2$–C$_{24}$-alkylacrylates, C$_2$–C$_{24}$-alkylmethacrylates and fluorinated derivatives thereof; styrene, substituted styrenes, such as dimethylaminomethylstyrene, 4-aminostyrene, 4-fluorostyrene, and pentafluorostyrene; ethylvinylbenzene; vinylnaphthalene; vinylpyridine; vinylimidazole; 4-vinylbiphenyl; and 4-vinylanisole.

The polymers in the polymer network can be cross-linked, for example, by incorporation of a multifunctional co-monomer. Suitable multifunctional co-monomers include diacrylates and dimethacrylates, such as ethylene glycol diacrylate, propylene glycol diacrylate, butylene glycol diacrylate, ethylene glycol dimethacrylate, butylene glycol dimethacrylate, methylene bis(methacrylamide), ethylene bis(acrylamide), ethylene bis(methacrylamide), ethylidene bis(acrylamide), ethylidene bis(methacrylamide), bisphenol A dimethacrylate and bisphenol A diacrylate. Other suitable multifunctional monomers include polyvinylarenes, such as divinylbenzene. The amount of cross-linking agent is typically between 0.5% and 25% by weight relative to the weight of the polymer, preferably from about 2.5% to about 20% by weight.

Polymers bearing amino groups can be cross-linked by bridging units between amino groups on adjacent polymer strands. Suitable bridging units include straight chain or branched, substituted or unsubstituted alkylene groups, diacylalkylene groups and diacylarene groups. Examples of suitable bridging units include —(CH$_2$)$_n$—, wherein n is an integer from about 2 to about 20, —CH$_2$—CH(OH)—

CH$_2$—, —C(O)CH$_2$CH$_2$C(O)—, —CH$_2$—CH(OH)—O—(CH$_2$)$_n$—O—CH(OH)—CH$_2$—, wherein n is 2 to about 4, and —C(O)—(C$_6$H$_2$(COOH)$_2$)—C(O)—. In preferred embodiments, the bridging unit comprises from about 0.5% to about 20% by weight of the polymer.

Advantageously, cross-linking the polymers renders the polymers non-adsorbable and stable. A "stable" polymer composition, when administered in therapeutically effective amounts, does not dissolve or otherwise decompose to form potentially harmful byproducts, and remains substantially intact so that it can transport ions out of the body following binding of bile acids.

Suitable polymer networks for administration include interpenetrating polymer networks and semi-interpenetrating polymer networks comprising polyallylamine/poly(N-isopropylacrylamide), polyallylamine/polystyrene and poly (allyl(n-decyl)amine/poly(trimethylammonioethylacrylate chloride).

The polymer network can be administered orally to a patient in a dosage of about 1 mg/kg/day to about 10 g/kg/day; the particular dosage will depend on the individual patient (e.g., the patient's weight and the extent of bile salt removal required). The polymer can be administered either in hydrated or dehydrated form, and can be flavored or added to a food or drink, if desired, to enhance patient acceptance. Additional ingredients such as other bile acid sequestrants, other drugs for treating hypercholesterolemia (such as a statin), atherosclerosis or other related indications, or inert ingredients, such as artificial coloring agents may be added as well.

Examples of suitable forms for administration include pills, tablets, capsules, and powders (i.e. for sprinkling on food). The pill, tablet, capsule or powder can be coated with a substance capable of protecting the composition from the gastric acid in the patient's stomach for a period of time sufficient for the composition to pass undisintegrated into the patient's small intestine. The polymer can be administered alone or in combination with a pharmaceutically acceptable carrier substance, e.g., magnesium carbonate or lactose.

Interpenetrating polymer networks for use in the method of the invention can be prepared via a variety of methods known in the art (Sperling, supra (1994)). For example, a cross-linked polymer can be formed from a first monomer. A second monomer, cross-linker and activating agent are then added to this polymer, swollen in an appropriate solvent, and the second monomer is polymerized and cross-linked in association with the first polymer. In another method, two or more monomers are mixed and simultaneously polymerized and cross-linked by non-interfering reactions. Alternately, two or more polymers are mixed and simultaneously cross-linked by non-interfering reactions. A semi-interpenetrating polymer network can be formed by a variation of one of these methods in which a cross-linking agent for at least one polymer is omitted.

Another method of forming an interpenetrating polymer network for administration involves mixing at least one monomer, at least one pre-formed non-cross-linked polymer and a cross-linking agent for each, and simultaneously polymerizing the monomer(s) and cross-linking via non-interfering reactions.

The monomer can be polymerized by methods known in the art, for example, via an addition process or a condensation process. In one embodiment, the monomer is polymerized via a free-radical process, and the reaction mixture preferably further comprises a free-radical initiator, such as a free radical initiator selected from among those which are well known in the art of polymer chemistry. Suitable free-radical initiators include azobis(isobutyronitrile), azobis(4-cyanovaleric acid), azobis(amidinopropane) dihydrochloride, potassium persulfate, ammonium persulfate and potassium hydrogenpersulfate. The free radical initiator is preferably present in the reaction mixture in an amount ranging from about 0.1 mole percent to about 5 mole percent relative to the monomer.

The choice of cross-linking agents depends upon the identity of the polymers to be cross-linked. Preferably, each polymer is cross-linked via different mechanisms, thereby ensuring that each polymer is cross-linked independently of the other(s). A polymer can be cross-linked, for example, by including a multifunctional co-monomer as the cross-linking agent in the reaction mixture. A multifunctional monomer can be incorporated into two or more growing polymer chains, thereby cross-linking the chains. Suitable multifunctional co-monomers include those discussed above. The amount of cross-linking agent added to the reaction mixture is, generally, between 0.5% and 25% by weight relative to the combined weight of the polymer and the cross-linking agent, and preferably from about 1% to about 10% by weight.

Polymers which comprise primary, secondary or tertiary amino groups can be cross-linked using a co-monomer as discussed above. Such polymers can also be cross-linked subsequent to polymerization by reacting the polymer with one or more cross-linking agents having two or more functional groups, such as electrophilic groups, which react with amine groups to form a covalent bond. Cross-linking in this case can occur, for example, via nucleophilic attack of the amino groups on the electrophilic groups. Suitable cross-linking agents of this type include compounds having two or more groups selected from among acyl chloride, epoxide, and alkyl-X, wherein X is a leaving group, such as a halo, tosyl or mesyl group. Examples of such compounds include epichlorohydrin, succinyl dichloride, butanedioldiglycidyl ether, ethanedioldiglycidyl ether, $\alpha,\omega$-polyethyleneglycoldiglycidyl ether, pyromellitic dianhydride and dihaloalkanes.

A polymer network comprising alkylated amino groups can be formed by reacting a polymer network, or a monomer thereof having primary, secondary or tertiary amino groups with a suitable alkylating agent. As used herein, the term "alkylating agent" refers to a compound which reacts with amino groups to form a nitrogen-carbon bond, thereby adding an alkyl or alkyl derivative substituent to the nitrogen atom. Suitable alkyl groups include normal or branched, substituted or unsubstituted $C_1$–$C_{24}$-alkyl groups, and suitable alkyl derivatives include arylalkyl, hydroxyalkyl, alkylammonium, and alkylamide groups.

Suitable alkylating agents are compounds comprising an alkyl group or alkyl derivative of the type listed above which is bonded to a leaving group, such as a halo, tosylate, mesylate or epoxy group. Examples of preferred alkylating agents include $C_1$–$C_{24}$-alkyl halides, for example, n-butyl halides, n-hexyl halides, n-decyl halides, and n-octadecyl halides; $C_1$–$C_{24}$-dihaloalkanes, for example, 1,10-dihalodecanes; $C_1$–$C_{24}$ hydroxyalkyl halides, for example, 11-halo-1-undecanols; $C_1$–$C_{24}$ arylalkyl halides, for example, benzyl halide; (halo-$C_1$–$C_{24}$-alkyl)ammonium salts, for example, 4-halobutyltrimethylammonium salts; $C_1$–$C_{24}$-alkyl epoxy ammonium salts, for example, glycidylpropyl-trimethylammonium salts; and $C_1$–$C_{24}$ epoxy alkylamides, for example, N-(2,3-epoxypropyl) butyramide or N-(2,3-epoxypropyl)hexanamide.

The extent of amino group alkylation can be controlled by controlling the stoichiometry of the alkylating agent. When the amino group is a primary or secondary amino group, it is possible that a given amino nitrogen atom will react with more than one molecule of the alkylating agent.

The invention will now be further and specifically described by the following examples.

EXAMPLES

Example 1

Preparation of a polyallylamine/poly(trimethylammonioethylacrylate) chloride interpenetrating polymer network To a 1-L round bottomed flask equipped with a magnetic stir-bar, a condenser and a nitrogen inlet tube was added poly(allylamine) hydrochloride (100 g of 50% aqueous solution; Nitto Boseki PAA-HCl-3L) and water (100 mL). To this solution was added 2-trimethylammonioethylacrylate chloride (TMAEAC) (Monomer-Polymer Labs) (100 g of a 50 wt % aqueous solution). The mixture was stirred to homogeneity and the pH was adjusted to ~9.8 with NaOH (50 wt % solution). The solution was degassed with a stream of nitrogen, and epichlorohydrin (1.46 g, 15.9 mmol, 3 mol % with respect to poly(allylamine)) was added. The mixture was stirred at room temperature for 15 minutes, followed by the addition of sodium bisulfite (0.7 g dissolved in 5 mL water). The solution was stirred for a further 10 minutes followed by the sequential addition of N,N'-methylenebisacrylamide (1.19 g, 0.79 mmol, 3 mol % with respect to TMAEAC). Finally a solution of potassium persulfate (0.7 g in 10 mL degassed water) was added and the polymerization mixture was allowed to stir for 18 h. The resulting gel was removed from the flask with a spatula and broken up in a kitchen blender. The gel was washed with isopropanol (3 L), dried in vacuo and the brittle solid was ground to a −30 mesh powder. Yield 73 g.

Example 2

Preparation of poly(allyl(n-decyl)amine)/poly (trimethylammonioethylacrylate) chloride interpenetrating polymer network To 20 g of interpenetrating polymer network of Example 1, suspended in 250 mL of methanol, was added 1-bromodecane (23.64 g, 107 mmol). The mixture was heated to 65° C., and a solution of NaOH (4.28 g, 107 mmol) in water (10 mL) was added in four portions at 2 h intervals. Heating was continued for a total of 18 h, the mixture was cooled and filtered and the off-white solid was washed with methanol (3×200 mL). The solid was stirred with 2N sodium chloride (500 mL) for 1 h and filtered. This step was repeated twice. The solid was finally washed with copious amounts of distilled water and dried in vacuo. Yield 21.7 g.

Example 3

Preparation of 3% Poly(allylamine/epichlorohydrin)

To a 4-L plastic beaker was added poly(allylamine) hydrochloride (2001.5 g of 50% aqueous solution; Nitto Boseki PAA-HCl-3L) and water (3 L). The mixture was stirred until homogeneous and the pH was adjusted to ~10.5 with solid NaOH (280.3 g). The pH was reduced by adding concentrated hydrochloric acid until the pH was ~10.2. The solution was allowed to cool to room temperature in the beaker and epichlorohydrin (25 mL; 29.1 g, 3 mole %) was added all at once with stirring. The mixture was stirred gently until it gelled and then was allowed to continue curing for 18 h at room temperature. The gel was then removed and broken up by passing it through a Kitchen Aid mixer. The solid was then suspended in ~16 L of deionized water. The gel was collected by filtration and washed on the funnel until the conductivity of the effluent was equal to 16.7 mS/cm. The solid was dried in a forced air oven at 60° C. for 5 days to yield 866.3 g of a granular, brittle, white solid. The solid was ground in a coffee grinder and passed through a 30 mesh sieve.

Example 4

Preparation of polyallylamine/styrene semi-interpenetrating polymer network

Poly(allylamine/epichlorohydrin) (3% crosslinking; 20 g) was suspended in water (1 L) containing sodium hydroxide (10 g). After stirring for 15 minutes the pH was 13.3. The solid was collected by filtration and rinsed on the funnel with three 1-L portions of water. The solid was dried in a forced air oven at 60° C. for 18 h to produce 13.9 g of deprotonated poly(allylamine/epichlorohydrin) as a white solid.

Deprotonated poly(allylamine/epichlorohydrin) (10 g) was added to a 250-mL Erlenmeyer flask. A solution containing acetonitrile (180 g), styrene (20 g), and azobisisobutyronitrile (AIBN, 0.2 g) was added slowly until it was no longer absorbed by the gel, leaving no excess fluid outside the particles. The flask was heated to reflux (80–88° C.) under a nitrogen atmosphere for 6 h. The mixture was then cooled to room temperature and methanol (600 mL) was added. The solution was stirred for 3 h, and the gel was collected by filtration. The gel was rinsed on the funnel with methanol (600 mL) and then water (2 L). The wet gel (61.4 g) was dried in a forced air oven at 60° C. for 18 h to yield 10.8 g of a dry solid.

Example 5

Preparation of polyallylamine/styrene semi-interpenetrating polymer network

Poly(allylamine/epichlorohydrin) (3% crosslinking; 20 g) was added to a 250-mL Erlenmeyer flask. A solution containing acetonitrile (180 g), styrene (20 g), and azobisisobutyronitrile (AIBN, 0.2 g) was added (13.3 g) slowly until it was no longer absorbed by the gel. At this point the remaining clear liquid (1.3 g) was removed, leaving only swollen gel. The flask was heated to reflux (80–88° C.) under a nitrogen atmosphere for 30 minutes. The mixture was then cooled to room temperature and methanol (600 mL) was added. The solution was stirred for 1 h, and the gel was collected by filtration. The gel was washed on the funnel with methanol (600 mL) and then water (2 L). The wet gel was dried in a forced air oven at 60° C. for 18 h to yield 18.6 g of a dry solid.

Example 6

Preparation of a polyallylamine/poly(N-isopropylacrylamide) interpenetrating polymer network To a 1-L round bottomed flask equipped with a magnetic stir-bar, a condenser and a nitrogen inlet tube was added poly(allylamine) hydrochloride (40 g of 50% aqueous solution; Nitto Boseki PAA-HCl-3L) and water (100 mL). To this solution was added N-isopropylacrylamide (20.0 g) (Aldrich). The mixture was stirred to homogeneity and the pH was adjusted to ~9.75 with NaOH (50 wt % solution). The solution was degassed with a stream of nitrogen and epichlorohydrin (0.59 g, 6.4 mmol, 3 mol % with respect to poly(allylamine) was added. The mixture was stirred at room temperature for 15 minutes, followed by the addition of N,N'-methylenebisacrylamide (0.82 g, 3 mol % with respect to N-isopropylacrylamide). A solution of ammonium persulfate (0.7 g in 10 mL degassed water) was added. An immediate reaction took place with the formation of a opaque white gel. The solution was allowed to react overnight, the gel was broken with a spatula and filtered. The sticky mass was washed with water, dried in a forced air oven at 60° C. A brittle off-white solid (33 g, 82.5%) was obtained.

Example 7

In vivo testing of polymer networks

Twenty-one male $F_1B$ Strain, Golden Syrian Hamsters, 8 weeks of age, were purchased from Biobreeders (Fitchburg, Mass.). Animals were allowed to acclimate to the facility for one week prior to use. Upon arrival and during the acclimation and study periods, the animals were placed in individual, stainless steel hanging cages fitted with individual water bottles. During the acclimation period animals were fed Purina Rodent pellets (#5001, Farmer's Exchange, Framingham, Mass.) and tap water, both ad libidum. During the study period, animals were provided water and fed Purina Rodent meal (#5001, Farmer's Exchange) containing mixed lipids as described below, with and without test articles.

The test articles were mixed into the diet as follows: The fat mixture was prepared in advance. The ingredients were obtained from Bioserv, Frenchtown, N.J. and consisted of:

54.5% Coconut oil—Catalog #G5200

44.5% Corn oil—Catalog #G5320

1% Cholesterol—Catalog #G5180

The coconut oil was heated to a complete liquid (>21° C.), shaken, poured into 1 liter beakers and heated on a (hot plate/stir plate) to about 80 degrees C. Crystalline cholesterol was added to the hot coconut oil and stirred until dissolved (approximately 1 hour). Residual cholesterol clumps were manually crushed with a glass stir bar. The coconut oil/cholesterol mixture was poured into a larger beaker containing the corn oil, resulting in a mixture containing 1 gram of cholesterol for each 100 grams of oil. The entire oil blend was well mixed prior to addition to the chow to prevent separation of different lipid types.

Two interpenetrating polymer networks, copoly (TMAEAC/allylamine) and copoly(TMAEAC/N-decylallylamine)(also referred to as drug) were mixed in the diet as a percent by weight of the dry-food and oil blend. Thus 5 kg of a 0.5% treatment diet contained:

25 grams of drug 0.5%

500 grams of oil blend 10%

4475 grams of powdered diet 89.5%

The drug was mixed into 1 kg of powdered diet thoroughly with a spoon, combined with another 1 kg of powdered diet and mixed thoroughly again. The 2 kg mixture was then combined with 2.48 kg of powdered diet and mixed again.

The diet-drug mixture was placed in a 20 quart mixer and mixed for 1 minute on low speed. The stirring oil blend (500 grams) was then added to the diet-drug mixture and mixed at higher speeds for about 4 to 5 minutes. Water was then added slowly to the diet while it was mixing to form a muddy consistency (approximately 700 mL/kg powdered diet); it is mixed as a mud for about 2 minutes. The diet was then pressed in a suitable container and then cut into 100–150 gram cakes and stored in a sealed Tupperware container at −20° C. for the duration of the study.

The hamsters were divided into three groups of 7 animals each. One group served as the control and was fed the high-fat diet without added polymer composition. Each of the other groups was served a diet including one of two interpenetrating polymer network compositions, copoly (TMAEAC/allylamine) and copoly(TMAEAC/N-decylallylamine), 0.5% by weight.

Animals were fasted 24 hours prior to blood collection. Animals were anesthetized with $O_2$:$CO_2$ 50:50. They were bled via the retro orbital sinus utilizing 250 $\mu$L (12 mm) heparinized capillary tubes (Drummond Scientific Co., Broomall, Pa., Cat #1-000-2500-LH/W). Blood was then transferred into a heparinized collection tube, which was closed and inverted repeatedly to ensure good mixing of blood and heparin. Plasma was isolated in a microfuge spun for 8 minutes at 12,400 rpm (13,600×g). Plasma was stored at 4° C. and analyzed within 24 hours.

Plasma total cholesterol was determined enzymatically using a Technicon RA-1000 System. The results are given as % Inhibition, the percent prevention of rise in cholesterol levels versus untreated controls, which was calculated according to:

$$\left\{1 - \left(\frac{\text{Treatment Mean Cholesterol} - 100^*}{\text{Control Mean cholesterol} - 100^*}\right)\right\} \times 100\%$$

*100 represents the total cholesterol level at baseline based on historical use of this model.

Tables 1–3, below, show the results of serum cholesterol measurements for each set of seven hamsters. The control set showed an increase in cholesterol level from week one to week two, and was relatively unchanged from week two to week three. The set of hamsters receiving the copoly (TMAEAC/allylamine) composition showed a smaller increase in mean serum cholesterol level after two weeks, with a % inhibition of 13.96, but after three weeks exhibited a % inhibition of 0.51%. The group receiving the copoly (TMAEAC/N-decylallylamine) composition showed a substantial decrease in mean serum cholesterol level after 2weeks, with a Winhibition of 66.74, with a slight increase in mean serum cholesterol level after 3 weeks, with a % inhibition of 64.56.

TABLE 1

| Control | | |
|---|---|---|
| HIGH FAT DIET WEEK 1 | WEEK 2 | WEEK 3 |
| 19 | 229 | 207 |
| 179 | 220 | 238 |
| 214 | 223 | 238 |
| 205 | 230 | 235 |
| 206 | 271 | 289 |
| 229 | 238 | 214 |
| 235 | 257 | 258 |
| mean: 198.1 | 238.3 | 239.9 |
| SD 39.4 | 18.9 | 27.5 |

TABLE 2

| copoly(TMAEAC/allylamine) | | |
|---|---|---|
| 1 WEEK HIGH FAT DIET | WK 1 TEST DIET ON POLYMER | WK 2 TEST DIET ON POLYMER |
| 135 | 166 | 168 |
| 176 | 213 | 233 |
| 202 | 215 | 271 |
| 203 | 232 | 279 |
| 209 | 217 | 232 |
| 223 | 227 | 220 |
| 240 | 263 | 271 |
| mean 198.3 | 219.0 | 239.1 |
| SD 34.2 | 29.0 | 39.0 |

TABLE 3

| Copoly (TMAEAC/N-decylallylamine) | | |
|---|---|---|
| 1 WEEK HIGH FAT DIET | WK 1 TEST DIET ON POLYMER | WK 2 TEST DIET ON POLYMER |
| 139 | 119 | 124 |
| 222 | 185 | 181 |
| 174 | 127 | 145 |
| 186 | 97 | 96 |
| 203 | 137 | 175 |

TABLE 3-continued

Copoly (TMAEAC/N-decylallylamine)

| 1 WEEK<br>HIGH FAT<br>DIET | WK 1<br>TEST<br>DIET<br>ON<br>POLYMER | WK 2<br>TEST<br>DIET<br>ON<br>POLYMER |
|---|---|---|
| 211 | 148 | 121 |
| 245 | 209 | 205 |
| Mean 197.1 | 146.0 | 149.6 |
| SD 34.6 | 38.9 | 38.9 |

EQUIVALENTS

Those skilled in the art will recognize or be able to ascertain using no more than routine experimentation many equivalents to the specific embodiments of the invention described herein. Such equivalents are intended to be encompassed in the scope of the following claims.

We claim:

1. A method for removing bile salts from a patient comprising the step of administering to the patient a therapeutically effective amount of an interpenetrating polymer network comprising a cationic polymer.

2. The method of claim 1 wherein the cationic polymer comprises substituted or unsubstituted amino or ammonium groups.

3. The method of claim 2 wherein the cationic polymer comprises amino groups having a substituent selected from the group consisting of straight chain or branched $C_2$–$C_{24}$-alkyl groups, arylalkyl groups, aminoalkyl groups and ammonioalkyl groups.

4. The method of claim 2 wherein the cationic polymer is substituted or unsubstituted polyvinylamine, polyallylamine or polyethyleneimine, or a salt thereof with a pharmaceutically acceptable acid.

5. The method of claim 2 wherein the cationic polymer is characterized by a repeat unit having the general formula

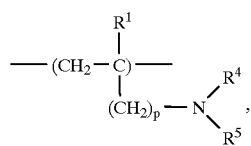

wherein p is an integer from about 0 to about 10, $R^1$ is hydrogen, methyl or ethyl, and $R^4$ and $R^5$ are each, independently, hydrogen or a substituted or unsubstituted alkyl; or salts thereof with a pharmaceutically acceptable acid.

6. The method of claim 2 wherein the cationic polymer is characterized by a repeat unit having the general formula

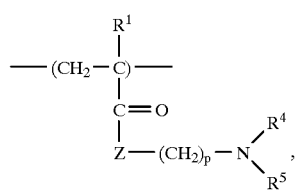

wherein Z is an oxygen atom or an $NR^7$ group; p is an integer from 1 to about 10; $R^1$ is hydrogen, methyl or ethyl; $R^7$ is hydrogen or alkyl; and $R^4$ and $R^5$ are each, independently, hydrogen or a substituted or unsubstituted alkyl or arylalkyl; or a salt thereof with a pharmaceutically acceptable acid.

7. The method of claim 2 wherein the cationic polymer is characterized by a repeat unit having the general formula

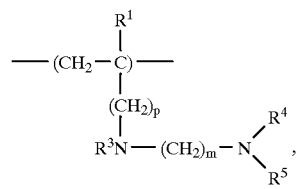

wherein p is an integer from 0 to about 10; m is an integer from 1 to about 10; $R^1$ is hydrogen, methyl or ethyl; $R^3$ is hydrogen or alkyl; and $R^4$ and $R^5$ are each, independently, hydrogen or a substituted or unsubstituted alkyl or arylalkyl group; or a salt thereof with a pharmaceutically acceptable acid.

8. The method of claim 3 wherein the cationic polymer is characterized by a repeat unit of the formula

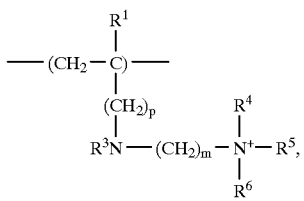

wherein p is an integer from 0 to about 10; m is an integer from 1 to about 10; $R^1$ is hydrogen, methyl or ethyl; $R^3$ is hydrogen or alkyl; and $R^4$, $R^5$ and $R^6$ are each a substituted or unsubstituted alkyl or arylalkyl group.

9. The method of claim 8 wherein $R^4$, $R^5$ and $R^6$ are each an alkyl group.

10. The method of claim 9 wherein $R^4$, $R^5$ and $R^6$ are each a methyl group.

11. The method of claim 2 wherein the cationic polymer is characterized by a repeat unit having the formula

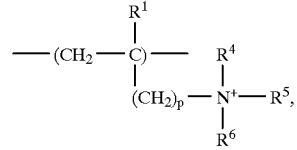

wherein p is an integer from 0 to about 10, $R^1$ is hydrogen, methyl or ethyl, and $R^4$, $R^5$ and $R^6$ are each a substituted or unsubstituted alkyl or arylalkyl group.

12. The method of claim 2 wherein the cationic polymer is characterized by a repeat unit having the formula

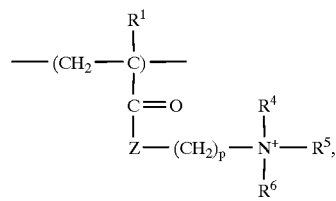

wherein Z is an oxygen atom or an $NR^7$ group; p is an integer from 1 to about 10; $R^1$ is hydrogen, methyl or ethyl; $R^7$ is hydrogen or an alkyl group; and $R^4$, $R^5$, and $R^6$ are each a substituted or unsubstituted alkyl or arylalkyl group.

13. The method of claim 12 wherein the cationic polymer is poly(trimethylammonioethylacrylate chloride) or poly (methacryloylaminopropyltrimethylammonium chloride).

14. The method of claim 2 wherein the cationic polymer is cross-linked.

15. The method of claim 14 wherein the cationic polymer is cross-linked by bridging units selected from the group consisting of straight chain or branched, substituted or unsubstituted alkylene groups, diacylalkylene groups and diacylarene groups.

16. The method of claim 15 wherein the cationic polymer is cross-linked by bridging units selected from the group consisting of —$(CH_2)_n$—, wherein n is an integer from about 2 to about 20, —$CH_2$—$CH(OH)$—$CH_2$—, —$C(O)$ $CH_2CH_2C(O)$—, —$CH_2$—$CH(OH)$—O—$(CH_2)_n$—O—$CH(OH)$—$CH_2$—, wherein n is 2 to about 4, and —$C(O)$—$(C_6H_2(COOH)_2)$—$C(O)$—.

17. A method for removing bile salts from a patient comprising the step of administering to the patient a therapeutically effective amount of an interpenetrating polymer network comprising a cationic polymer and a hydrophobic polymer.

18. The method of claim 17 wherein the hydrophobic polymer comprises a monomer selected from the group consisting of N—$C_2$-$C_{24}$-alkylacrylamides; fluorinated N—$C_2$-$C_{24}$-alkylacrylamides; N—$C_2$-$C_{24}$-alkylmethacrylamides; fluorinated N-$C_2$-$C_{24}$-alkylmethacrylamides; $C_2$-$C_{24}$-alkylacrylates; fluorinated $C_2$-$C_{24}$-alkylacrylates; $C_2$-$C_{24}$-alkylmethacrylates; fluorinated $C_2$-$C_{24}$-alkylmethacrylates; styrene; substituted styrenes; ethylvinylbenzene; vinylnaphthalene; vinylpyridine; vinylimidazole; 4-vinylbiphenyl; and 4-vinylanisole.

19. The method of claim 17 wherein the hydrophobic polymer is characterized by a repeat unit which includes a $C_2$-$C_{24}$-alkyl-substituted amino group.

20. The method of claim 17 wherein the hydrophobic polymer is cross-linked.

21. The method of claim 20 wherein the hydrophobic polymer is cross-linked by a multifunctional co-monomer.

22. The method of claim 21 wherein the multifunctional co-monomer is selected from the group consisting of diacrylates, dimethacrylates and polyvinylarenes.

23. The method of claim 22 wherein the multifunctional monomer is selected from the group consisting of ethylene glycol diacrylate, propylene glycol diacrylate, butylene glycol diacrylate, ethylene glycol dimethacrylate, butylene glycol dimethacrylate, methylene bis(methacrylamide), methylene bis(acrylamide) ethylene bis(acrylamide), ethylene bis(methacrylamide), ethylidene bis(acrylamide), ethylidene bis(methacrylamide), bisphenol A dimethacrylate, bisphenol A diacrylate and divinylbenzene.

24. The method of claim 19 wherein the hydrophobic polymer is selected from the group consisting of N—$C_2$-$C_{24}$-alkyl-substituted polyvinylamines, $C_2$-$C_{24}$-alkyl-substituted polyallylamines and $C_2$-$C_{24}$-alkyl-substituted polyethyleneimines.

25. The method of claim 17 wherein the cationic polymer comprises substituted or unsubstituted amino or ammonium groups.

26. The method of claim 25 wherein the cationic polymer is substituted or unsubstituted polyvinylamine, polyallylamine or polyethyleneimine, or a salt thereof with a pharmaceutically acceptable acid.

27. The method of claim 25 wherein the cationic polymer comprises amino groups having a substituent selected from the group consisting of straight chain or branched $C_2$-$C_{24}$-alkyl groups, arylalkyl groups, aminoalkyl groups and ammonioalkyl groups.

28. The method of claim 25 wherein the cationic polymer is characterized by a repeat unit having the general formula

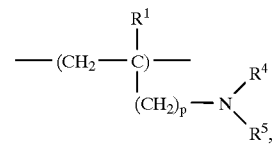

wherein p is an integer from about 0 to about 10; $R^1$ is hydrogen, methyl or ethyl; and $R^4$ and $R^5$ are each, independently, hydrogen or a substituted or unsubstituted alkyl or arylalkyl group; or salts thereof with a pharmaceutically acceptable acid.

29. The method of claim 25 wherein the cationic polymer is characterized by a repeat unit having the general formula

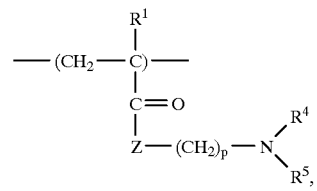

wherein Z is an oxygen atom or an $NR^7$ group, p is an integer from 1 to about 10, $R^1$ is hydrogen, methyl or ethyl; $R^7$ is hydrogen or alkyl; and $R^4$ and $R^5$, are each, independently, hydrogen or a substituted or unsubstituted alkyl; or a salt thereof with a pharmaceutically acceptable acid.

30. The method of claim 27 wherein the cationic polymer is characterized by a repeat unit having the general formula

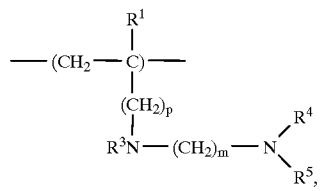

wherein p is an integer from 0 to about 10; m is an integer from 1 to about 10; $R^1$ is hydrogen, methyl or ethyl; $R^3$ is hydrogen or alkyl; and $R^4$ and $R^5$ are each, independently, hydrogen or a substituted or unsubstituted alkyl or arylalkyl group; or a salt thereof with a pharmaceutically acceptable acid.

31. The method of claim 27 wherein the cationic polymer is characterized by a repeat unit of the formula

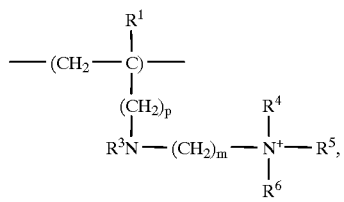

wherein p is an integer from 0 to about 10; m is an integer from 1 to about 10; $R^1$ is hydrogen, methyl or ethyl; $R^3$ is hydrogen or alkyl; and $R^4$, $R^5$ and $R^6$ are each a substituted or unsubstituted alkyl or arylalkyl group.

32. The method of claim 25 wherein the cationic polymer is characterized by a repeat unit having the formula

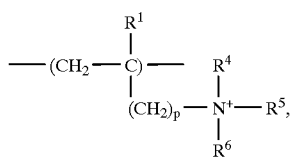

wherein p is an integer from 0 to about 10; $R^1$ is hydrogen, methyl or ethyl; and $R^4$, $R^5$ and $R^6$ are each a substituted or unsubstituted alkyl or arylalkyl group.

33. The method of claim 25 wherein the cationic polymer is characterized by a repeat unit having the formula

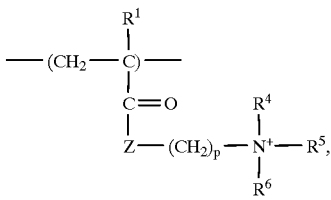

wherein Z is an oxygen atom or an $NR^7$ group; p is an integer from 1 to about 10; $R^1$ is hydrogen, methyl or ethyl; $R^7$ is hydrogen or an alkyl group; and $R^4$, $R^5$, and $R^6$ are each a substituted or unsubstituted alkyl or arylalkyl group.

34. The method of claim 33 wherein the cationic polymer is poly(trimethylammonioethylacrylate chloride) or poly(methacryloylaminopropyltrimethylammonium chloride).

35. A method for removing bile salts from a patient comprising the step of administering to the patient a therapeutically effective amount of an interpenetrating polymer network comprising a quaternary ammonium-substituted polymer and an amine-substituted polymer having a hydrophobic backbone.

36. The method of claim 35 wherein the quaternary ammonium-substituted polymer is poly(trimethylammonioethylacrylate chloride) or poly(methacryloylaminopropyltrimethylammonium chloride).

37. The method of claim 35 wherein the amine-substituted polymer is selected from the group consisting of poly(allylamine), poly(vinylamine) or poly(ethyleneimine).

38. The method of claim 35 wherein the amine-substituted polymer is characterized by a repeat unit having the formula

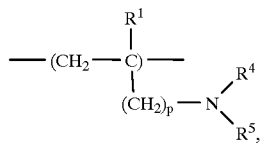

wherein p is an integer from 0 to about 10, $R^1$ is hydrogen, methyl or ethyl, and $R^4$ and $R^5$ are each, independently, hydrogen or a substituted or unsubstituted alkyl or arylalkyl group; or salts thereof with a pharmaceutically acceptable acid.

39. The method of claim 35 wherein the amine-substituted polymer is characterized by a repeat unit having the general formula

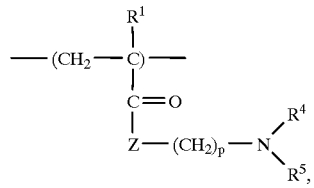

wherein Z is an oxygen atom or an $NR^7$ group; p is an integer from 1 to about 10; $R^1$ is hydrogen, methyl or ethyl; $R^7$ is hydrogen or an alkyl group; and $R^4$ and $R^5$ are each, independently, hydrogen or a substituted or unsubstituted alkyl or arylalkyl group; or salts thereof with a pharmaceutically acceptable acid.

40. The method of claim 35 wherein the amine-substituted polymer comprises amino groups having a substituent selected from the group consisting of straight chain or branched $C_2$–$C_{24}$-alkyl groups, arylalkyl groups, aminoalkyl groups and ammonioalkyl groups.

41. The method of claim 40 wherein the polymer having amino groups is characterized by a repeat unit having the formula

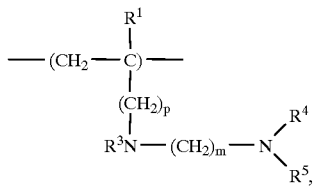

wherein p is an integer from 0 to about 10; $R^1$ is hydrogen, methyl or ethyl; m is an integer from 1 to about 10; $R^3$ is hydrogen or alkyl; and $R^4$ and $R^5$ are each, independently, hydrogen or methyl; or a salt thereof with a pharmaceutically acceptable acid.

42. The method of claim 35 wherein the interpenetrating polymer network comprises poly(trimethylammonioethylacrylate chloride) and poly(allylamine).

43. The method of claim 41 wherein the interpenetrating polymer network comprises poly(trimethylammonioethylacrylate chloride) and poly(allylamine-co-N-(n-decyl)allylamine).

* * * * *